US010942161B2

(12) United States Patent
Vann et al.

(10) Patent No.: US 10,942,161 B2
(45) Date of Patent: Mar. 9, 2021

(54) ELECTROSTATIC VARNISH AND PRECURSOR DETECTION IN LUBRICANTS

(71) Applicant: ExxonMobil Research and Engineering Company, Annandale, NJ (US)

(72) Inventors: Walter D. Vann, Green Castle, PA (US); Kathleen K. Cooper, South River, NJ (US); Spyridon Korres, Hamburg (DE); Samuel Flores-Torres, Burlington, NJ (US); Bhaskar Prabhakar, Mount Laurel, NJ (US); Erik Herz, Conroe, TX (US)

(73) Assignee: EXXONMOBIL RESEARCH AND ENGINEERING COMPANY, Annandale, NJ (US)

( * ) Notice: Subject to any disclaimer, the term of this patent is extended or adjusted under 35 U.S.C. 154(b) by 126 days.

(21) Appl. No.: 16/123,089

(22) Filed: Sep. 6, 2018

(65) Prior Publication Data

US 2019/0086383 A1 Mar. 21, 2019

Related U.S. Application Data

(60) Provisional application No. 62/558,911, filed on Sep. 15, 2017.

(51) Int. Cl.
*G01N 33/28* (2006.01)
*C10M 175/00* (2006.01)
(Continued)

(52) U.S. Cl.
CPC ... *G01N 33/2888* (2013.01); *C10M 175/0066* (2013.01); *G01N 21/25* (2013.01);
(Continued)

(58) Field of Classification Search
CPC .................................................. G10N 33/2888
See application file for complete search history.

(56) References Cited

U.S. PATENT DOCUMENTS 6,061,139 A * 5/2000 Takezawa .......... G01N 21/3151
356/407
6,151,108 A 11/2000 Kwon et al.
(Continued)

FOREIGN PATENT DOCUMENTS

EP 2505999 A1 3/2012

OTHER PUBLICATIONS

International Search Report and Written Opinion PCT/US2018/049654 dated Nov. 20, 2018.

*Primary Examiner* — Paul M. West
*Assistant Examiner* — Mark A Shabman
(74) *Attorney, Agent, or Firm* — Anthony G. Boone

(57) ABSTRACT

Methods are provided for in-situ detection of varnish and/or deposit precursors in a lubricant in a lubricating environment. An electrostatic accumulator can be used within a lubricating environment to enhance accumulation of varnish and/or deposit precursors on portions of the electrostatic accumulator. The deposits accumulated on the electrostatic accumulator can then be characterized in-situ. The potential difference across portions of the electrostatic accumulator can cause an enhanced rate of deposit accumulation on the electrostatic accumulator, which can facilitate characterization of the tendency of a lubricant to accumulate deposits in the lubricating environment.

18 Claims, 6 Drawing Sheets

(51) Int. Cl.
  *G01N 21/25*  (2006.01)
  *G01N 27/60*  (2006.01)
  *G01N 33/30*  (2006.01)
  *C10N 30/04*  (2006.01)
  *C10N 30/00*  (2006.01)

(52) U.S. Cl.
  CPC .............. *G01N 27/60* (2013.01); *G01N 33/30* (2013.01); *C10N 2030/04* (2013.01); *C10N 2030/72* (2020.05)

(56) References Cited

U.S. PATENT DOCUMENTS

| | | | |
|---|---|---|---|
| 6,774,645 B1 * | 8/2004 | Leidl | G01N 33/2858 |
| | | | 324/658 |
| 7,744,739 B1 | 6/2010 | Green | |
| 8,935,910 B2 | 1/2015 | Cournoyer et al. | |
| 2012/0086942 A1 * | 4/2012 | Honda | G01N 21/27 |
| | | | 356/436 |
| 2012/0229151 A1 * | 9/2012 | Katafuchi | G01N 33/2888 |
| | | | 324/672 |
| 2014/0007657 A1 | 1/2014 | Matsubara et al. | |
| 2016/0252490 A1 | 9/2016 | Shirata et al. | |
| 2018/0003618 A1 * | 1/2018 | Shinoda | G01N 21/94 |

* cited by examiner

ELECTROSTATIC VARNISH AND PRECURSOR DETECTION IN LUBRICANTS

CROSS-REFERENCE TO RELATED APPLICATIONS

This application claims the benefit of U.S. Provisional Application No. 62/558,911, filed on Sep. 15, 2017, the entire contents of which are incorporated herein by reference.

FIELD

This invention relates to systems and methods involving an electrostatic accumulator for in-situ detection of varnish and other deposit precursors in a lubricant.

BACKGROUND

Formation of varnish and/or other deposits on surfaces is a known problem for lubricants in many lubricating environments. Accumulation of such deposits on lubricating environment surfaces can lead to unexpected pressure changes and/or flow disruptions for lubricants within a lubricating environment. Various efforts have been made to reduce such deposits or otherwise reduce the likelihood of deposits causing problems.

It is conventionally believed that precursors that form within a lubricant can contribute to formation of varnish or other deposits. Some methods for mitigating the problem of deposit formation have focused on removing the precursors from the lubricant prior to forming a deposit. Electrostatic accumulators are an example of a system component that has been used to remove deposit precursors. Lubricants are generally non-polar fluids while many types of deposit precursors correspond to compounds and/or particles that have polarity or are susceptible to becoming charged. An electrostatic accumulator in the flow path of the lubricant in the engine environment can attract such compounds and/or particles to the surface of the accumulator. The accumulator surface can then be periodically cleaned, such as after removal of the electrostatic accumulator from the engine environment. U.S. Pat. No. 8,935,910 provides an example of the use of electrostatic accumulators in an engine environment for removal of oil degradation byproducts. U.S. Pat. No. 7,744,739 provides an example of an electrostatic oil cleaner.

Other types of mitigation methods have focused on detection of precursor compounds within the lubricant. U.S. Pat. No. 6,151,108 describes an ex-situ method for detecting particles and iron content in a sample of a lubricating oil. U.S. Patent Application Publication 2016/0252490 describes an in-situ a lubricant deterioration sensor and optical sensor. The deterioration sensor includes a logarithmic amplifier instead of a linear amplifier to allow for detection of deterioration in a lubricant when the transmissivity of the lubricant is low.

U.S. Pat. No. 6,774,645 describes a device and method for detecting deposit formations on sensor surfaces where lubricants cause the formations. The device and method involve creating a potential difference between the surface of a sensor element and a lubricant (or optionally between the sensor element and the engine surfaces.) The potential difference between the sensor element and the lubricant can allow for increased deposition on the sensor element. It is noted that applying an opposing potential difference can then remove the deposits formed due to the initial potential difference. A physical parameter of the lubricant, as detected by the sensor element, can then be evaluated in a state when the sensor element has a potential difference relative to the lubricant and in a state without a potential difference, in order to determine whether the lubricant causes a deposit formation on the sensor surface.

SUMMARY

In various aspects, methods are provided for characterizing a lubricant oil in a lubricating environment. The methods can include passing a lubricant oil through a volume in a lubricating environment. The volume can have a surface that includes an electrostatic accumulator. The surface that includes the electrostatic accumulator can correspond to any convenient surface, such as a surface in a side stream volume or slip stream volume in the lubricating environment. The lubricating environment can correspond to any convenient lubricating environment, such as an engine environment, a turbine environment, or a machine environment. While passing a lubricant oil through the volume in the lubricating environment, a potential difference can be applied between at least a first portion of the electrostatic accumulator and a second portion of the electrostatic accumulator for a measurement period of time. After the measurement period of time, at least a portion of the electrostatic accumulator can be characterized while maintaining the electrostatic accumulator as a surface of the volume in the lubricating environment.

Optionally, additional characterizations can be performed on the electrostatic accumulator during the measurement period of time. Optionally, a plurality of measurement periods of time can be used, with measurements performed during and/or after each measurement period of time. In such an optional aspect, the potential difference between the portions of the electrostatic accumulator may be removed during at least a portion of the interim period between the measurement periods of time. Optionally, it may be desirable to characterize the electrostatic accumulator in a reference state prior to passing oil through the volume.

In some aspects, the characterizing of the at least a portion of the electrostatic accumulator can correspond to optical characterization, mechanical characterization, electrical characterization, or a combination thereof. Examples of optical characterization can include, but are not limited to, determining a Total Color Difference value for at least a portion of the electrostatic accumulator and determining a strip density for at least a portion of the electrostatic accumulator.

In some aspects where characterization includes determining Total Color Difference value(s), a Total Color Difference value can be used as an absolute value for comparison with one or more threshold values. In some aspects a Total Color Difference value can be compared with a second Total Color Difference value from a reference state, and the difference between the compared values can be compared with one or more threshold values.

DETAILED DESCRIPTION OF THE EMBODIMENTS

Overview

Figure 1:
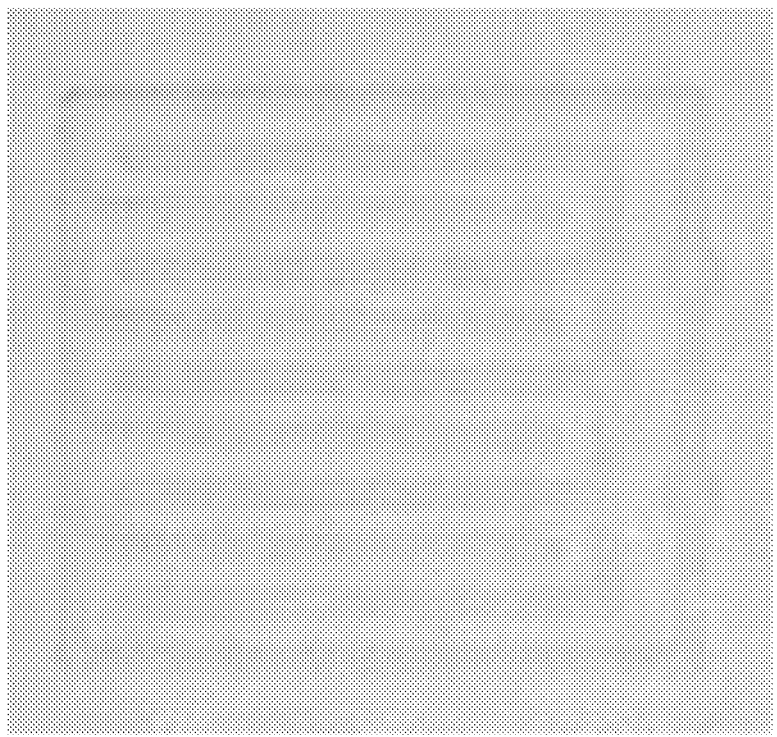
FIG. 1 shows an image of an electrostatic accumulator.

In various aspects, systems and methods are provided for in-situ detection of varnish and/or deposit precursors in a lubricant in a lubricating environment. An electrostatic accumulator can be used within a lubricating environment to enhance accumulation of varnish and/or deposit precursors on portions of the electrostatic accumulator. The deposits accumulated on the electrostatic accumulator can then be characterized in-situ. Without being bound by any particular theory, it is believed that using an electrostatic accumulator can increase the rate of deposit accumulation on the accumulator surface, relative to the rate of accumulation on a surface without a voltage (potential) difference. This increased rate of deposit accumulation can allow for characterization of an expected lifetime for the lubricant prior to needing a change of the lubricant.

Deposits are constituents which are not desirable in lubricating oils. They attribute to negative effects in oil lubrication systems. Terms that can be used to characterize deposits include sludge, varnish, insolubles, oxidative by products, polymerized oil, dirt and contaminants. Sludge and varnish can be generally distinguished by their consistency. Sludge is typically described as a thick, waxy, resinous, grease-like material can be wiped away. Varnish, while it may be sticky, is typically regarded as not being easily removed without solvent or other means. Precursors to deposits can contribute to both sludge or varnish outcomes. Wear and other contaminants can accelerate and contribute to deposit formation.

Potential problems from deposits can include, but are not limited to: formation of particles that interfere with other components function and are abrasive or sticky; restriction and sticking of moving mechanical parts valves, pistons; increased wear due as a result of varnish attracting contaminants; increased costs due to equipment cleanup & oil disposal; loss of heat transfer in heat exchangers; increased friction, heat and energy due to varnish's thermal insulation effect; deterioration of the lubricant; and plugging of orifices and/or reduction in filtration efficiency.

Conventional methods of deposit detection on lubricated surfaces typically involve laboratory analysis of the lubricant, visual inspection of the machinery (or other lubricating environment) containing the lubricant, and/or detecting pressure changes within the lubricating environment. These conventional methods present a variety of difficulties with regard to determining how and when to perform maintenance on machinery/engines/equipment associated with a lubricating environment. For example, laboratory analysis of a lubricant, while effective, can be a slow process that often involves equipment not available at the site where a machine (such as a turbine or engine) is being maintained. The nature of varnish and/or other deposit accumulation can also present difficulties, as the normal buildup of deposit materials in a lubricated environment can be both slow and random. Thus, the location of the largest buildup of deposit materials in a lubricated environment may not be easy to predict, which can pose risks if deposit detection is performed at a location that happens to have a randomly lower accumulation of deposited material. Additionally, for both visual inspection and detection of pressure changes, by the time visual deposits have formed and/or pressures within machinery have been changed in a statistically meaningful way, there may already be a risk of machine failure due to the varnish or deposits.

One or more of the above difficulties with current detection methods can be overcome by using an electrostatic accumulator to enhance accumulation of deposits onto the accumulator surface. This can allow for an increased rate of deposit accumulation at location(s) on the electrostatic accumulator surface. Rather than having the highest amount of deposit accumulation at a random or semi-random location, the enhanced rate of deposit accumulation can occur at a known location to allow for characterization. Because the location(s) of the enhanced accumulation are known, additional features can be incorporated into the lubricating environment to allow for characterization of the electrostatic accumulator. For example, when using an optical detection method, the electrostatic accumulator can optionally be located in a side stream or slip stream pathway in the lubricating environment. Additionally or alternately, an optically transparent window can be included on a surface opposing the location(s) of the electrostatic accumulator to allow for in-situ characterization.

Characterizing one or more locations of enhanced and/or increased deposit accumulation can allow, for example, development of a maintenance schedule that is specific to the conditions in a particular lubricating environment. Additionally, replacement of the lubricant in a lubricating environment can be performed at an extended lifetime without requiring the risk of having observable deposits and/or meaningful pressure changes within the environment.

In some aspects, a metric such as Total Color Difference can be used to characterize the amount of deposit accumulation on an electrostatic accumulator. It has been unexpectedly discovered that when an electrostatic accumulator is activated by applying a potential difference across the accumulator, the increased rate of deposit accumulation can allow the accumulator to quickly develop a difference in color (based on deposits) that is representative of the nature of the lubricating oil. While some additional color difference can develop over time, the Total Color Difference value for the electrostatic accumulator can approach an asymptotic limit based on the nature of the lubricating oil in less than 48 hours, or less than 24 hours, or less than 20 hours, or less than 12 hours. This can allow the electrostatic accumulator to be activated intermittently, as opposed to constantly remaining activated. For example, the electrostatic accumulator could be activated on a schedule, such as once a week or once a month, to allow for characterization of any changes in the tendency of the lubricant oil to form deposits. The period of activation for the electrostatic accumulator can correspond to a measurement period of time, such as 1 hour to 48 hours, or 4 hours to 24 hours, or 2 hours to 20 hours, or 1 hour to 12 hours. The Total Color Difference value for the electrostatic accumulator can then be determined and compared with a Total Color Difference value for suitable reference state. It is noted that multiple Total Color Difference values can potentially be collected during a single measurement period of time by collecting one or more values while the electrostatic accumulator remains activated.

The methodology for determining a Total Color Difference value can correspond to an adaptation of the membrane patch colorimetry (MPC) test specified in ASTM D7843. The MPC test measures color bodies of insoluble contaminants in lubricants using solvent extraction to capture oxidized insoluble material from used oil samples. The method described in ASTM D7843 involves holding the sample for a specified time at controlled temperature. A portion of the oil is mixed with a non-polar solvent and passed through a 0.45 micron Millipore patch. Varnish tends to be polar and is not very soluble where it collects on the patch. Under the procedure specified in ASTM D7843, the color of the oil (e.g., varnish, oxidized products, contaminants) collected on the patch is analyzed with a spectrophotometer to assess the total amount of color. Varnish tends to color the patch, where hue and intensity can be determined and make an assessment of the varnish level in the used oil. The patch is examined by a spectrophotometer where color differences are compared to a white background. Color values are captured using CIE uniform color space and color-difference equation. CIE tristimulus values measure light intensity based on the three primary color values (RGB), typically represented by X, Y, and Z coordinates.

Although ASTM D7843 is directed to characterization of color differences on a membrane, it has been discovered that the method for determining color differences specified in ASTM D7843 can also be used to characterize color changes on the surface of an electrostatic accumulator. The "Total Color Difference" as used herein corresponds to "$\Delta E$" as determined based on changes in the CIE tristimulus values as specified in ASTM D7843. Briefly, as described in ASTM D7843, the CIE color space corresponds to an approximately uniform color space. The system is defined by ASTM Practice E308. It is produced by plotting in rectangular coordinates the quantities L*, a*, b*. The tristimulus values Xn, Yn, Zn define the color of the normally white object-color stimulus. Under these conditions, Xn, Yn, and Zn are the tristimulus values of the standard 10° observer, D65 illuminant. The total difference delta E*ab between two colors each given in terms of L*, a*, b* is calculated. Delta E is the distance between colors and that a value of 1.0 is the smallest difference observable by the human eye.

In order to apply the color determination methods of ASTM D7843 to an electrostatic accumulator as described herein, a white object-color stimulus can still be used. Such a white object-color stimulus can correspond to the type of membrane specified in ASTM D7843, or any other convenient white stimulus. Total Color Difference values (i.e., $\Delta E$ values) can then be determined for a reference state of an electrostatic accumulator and one or more states of interest. In this discussion, a Total Color Difference value refers to a value that corresponds to the Total Color Difference relative to a white object-color stimulus, according to ASTM D7843. When a Total Color Difference value from a first state of an electrostatic accumulator is compared with a Total Color Difference value from a reference state, the comparison can also be referred to as determining a change in the Total Color Difference value relative to the reference state.

Based on obtaining a new Total Color Difference value, an evaluation can be made as to whether the lubricant oil in a machine has degraded to a point where maintenance should be performed, either in the near term or at a future date. For example, one option for characterizing the new Total Color Difference value can be based on a comparison of the new Total Color Difference with a prior Total Color Difference value for the electrostatic accumulator. If the change in Total Color Difference between successive measurements is greater than a first threshold value, such as greater than 50,000, or greater than 100,000, the deterioration of the lubricant oil can indicate that rapid deterioration is occurring and that a change or cleaning of the lubricant oil should occur in the near future. Additionally or alternately, a change in Total Color Difference of between 10,000 and 50,000 can indicate that deterioration is occurring, and that the magnitude of the change can be used to determine a future time when change or cleaning of the lubricant oil will be beneficial. The prior Total Color Difference value can correspond to a Total Color Difference value obtained for a reference state, such as a reference state corresponding to a prior activation of the electrostatic accumulator, a reference state corresponding to a prior time during the current activation of the electrostatic accumulator, or any other convenient reference state. It is noted that the threshold values provided above are representative. It may be beneficial to develop threshold values based on and/or specific to the configuration of a lubricating environment.

As another example, it may be beneficial to characterize a Total Color Difference value relative to the Total Color Difference value for a reference state that corresponds to a clean state of the electrostatic accumulator. The "clean" reference state can correspond to a time prior to exposure of the electrostatic accumulator to oil, a time prior to activation of the electrostatic accumulator, a state during activation of the electrostatic accumulator in the presence of clean oil, or another convenient reference state. When a Total Color Difference value is obtained and compared with the value for a clean state and/or another type of initial state for the electrostatic accumulator, a change in the Total Color Difference value that is greater than a threshold value of 200,000, or greater than 300,000, can indicate that rapid deterioration is occurring and that a change or cleaning of the lubricant oil should occur in the near future. Additionally or alternately, a change in the Total Color Difference of between 100,000 and 200,000 can indicate that deterioration is occurring, and that the magnitude of the change can be used to determine a future time when change or cleaning of the lubricant oil will be beneficial.

As still another example, it may be beneficial to use the magnitude of the Total Color Difference value, so that the "reference" value corresponds to the white object-color stimulus. When the white object-color stimulus is used as the reference value, a change in the Total Color Difference value that is greater than a threshold value of 500,000, or greater than 700,000, can indicate that rapid deterioration is occurring and that a change or cleaning of the lubricant oil should occur in the near future. Additionally or alternately, a change in the Total Color Difference of between 300,000 and 500,000 can indicate that deterioration is occurring, and that the magnitude of the change can be used to determine a future time when change or cleaning of the lubricant oil will be beneficial.

In some optional aspects, when attempting to characterize the aging of a lubricant oil based on a change in a Total Color Difference value relative to the Total Color Difference value for a reference state (such as a reference state corresponding to a clean or substantially clean state of the electrostatic accumulator), it may be beneficial to determine a Total Color Difference value for an intermediate reference state corresponding to exposing the electrostatic accumulator to a clean oil for period of time corresponding to the measurement period of time. For example, if a reference state is selected where oil is not present in the in-situ environment, simply adding any lubricant oil may result in a large Total Color Difference value. By using a second or intermediate reference state, the portion of the Total Color Difference value that is related to the nature of the lubricant oil and/or the machine environment can be subtracted out. Due to variations in the color of various types of lubricant oils, being able to subtract out a background portion of the Total Color Difference value that is due to the nature of the oil can assist with selecting threshold values for determination of the amount of degradation for the lubricant oil. Similarly, the change in color value between the white-object color stimulus and the electrostatic accumulator may correspond to a large Total Color Difference value. This difference can optionally be subtracted out as a background value if desired when determining appropriate threshold values for determination of the amount of degradation for the lubricating oil.

In this discussion, a lubricant can refer to a non-polar hydrocarbon or hydrocarbon-like fluid that is used within a lubricating environment to provide lubrication. In some aspects, the lubricating environment can correspond to a turbine, such as a gas turbine. In some aspects, the lubricating environment can correspond to an engine. In some aspects, the lubricating environment can correspond to a machine environment.

Optical Characterization of Enhanced Deposit Accumulation

FIG. 1 shows an example of an electrostatic accumulator surface 100 that can be incorporated into a lubricating environment to allow for enhanced accumulation of deposits. In FIG. 1, the external conductive lines 110 (including the connected prongs) can be charged to create a potential difference relative to the internal conductive lines 120. Any convenient potential difference can be used. In some aspects, the internal conductive lines 120 can be at a ground potential, while in other aspects a positive or negative charge can also be applied to internal conductive lines 120 in order to create a desired potential difference between internal conductive lines 120 and external conductive lines 110.

FIG. 1 shows an optical image of electrostatic accumulator surface 100 in a clean state prior to any accumulation of deposits on the surface. The image in FIG. 1 was obtained by exposing the electrostatic accumulator surface 100 to fresh oil for a short period of time without applying a potential difference between external conductive lines 110 and internal conductive lines 120. The image was obtained in-situ via an optically transparent window in the lubricating environment. For Total Color Difference value measurements, a spectrophotometer was also used to perform in-situ characterization.

Electrostatic accumulators of the type shown in FIG. 1 were exposed to various lubricating oils in a test apparatus. A potential difference of about 1 to 50 kiloVolts can be applied between the external conductive lines 110 and internal conductive lines 120 while exposing the electrostatic accumulator to a flow of each lubricating oil. The choice of potential difference can vary depending on the nature of the volume containing the lubricating oil and the flow rate (if any) of the lubricating oil through the volume. A first lubricating oil corresponded to a clean oil. A second oil was an oil that had resulted in light deposit formation in an engine environment. A third oil was an oil that had resulted in medium deposit formation in an engine environment. A fourth oil had resulted in heavy deposit formation in an engine environment. The accumulators were exposed to the various oils for 20 hours with a potential difference applied to the accumulators.

Figure 2:
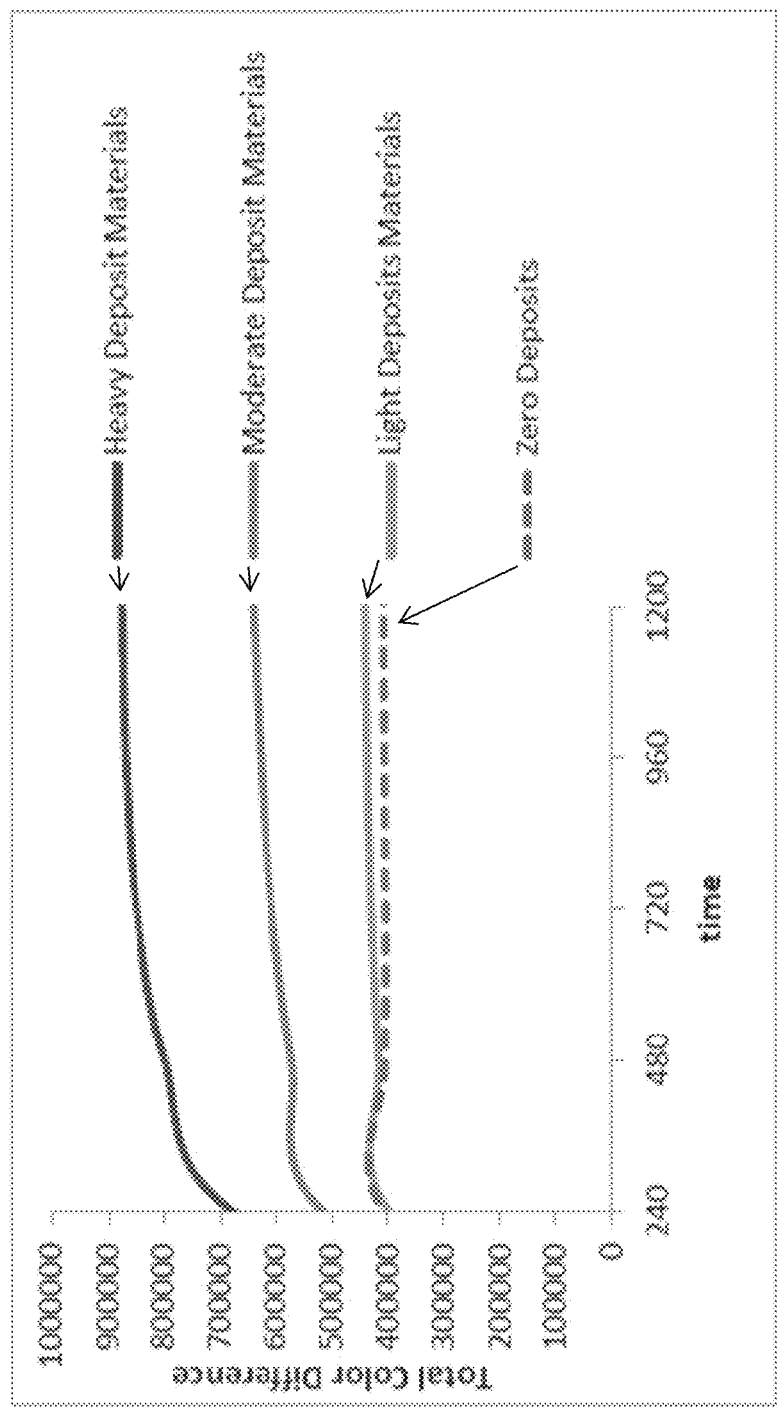
FIG. 2 shows Total Color Difference for electrostatic accumulators exposed to various lubricant oils while a potential difference is applied to the electrostatic accumulator.

An optical detector was used to measure the Total Color Difference in the accumulators before and after exposure to each lubricating oil. FIG. 2 shows the measured Total Color Difference for exposure to each lubricating oil. FIG. 2 provides several features of interest with regard to using optical detection as a method for characterizing deposits on an electrostatic accumulator. In FIG. 2, the first measurement time displayed corresponds to 240 minutes, or 4 hours after the activation of the electrostatic accumulator. Based on the values in FIG. 2, it appears that 4 hours provided a sufficient amount of deposit formation for the Total Color Difference values to start to approach asymptotic limits. In other words, the initial data points for each lubricant oil (after 4 hours of activation) appear to be indicative of the ability of the lubricant oil to form deposits. The additional data points up to 20 hours do result in some additional change in the Total Color Difference value, so in some aspects it could be beneficial to maintain activation of the electrostatic accumulator for a longer period.

Another feature of the data provided in FIG. 2 is that exposure of the electrostatic accumulator to a known "clean" oil results in a substantial Total Color Difference relative to a white object-color stimulus. This indicates that some portion of the Total Color Difference corresponds to color change that is inherent to the nature of the electrostatic accumulator and/or the nature of the lubricant oil. In other words, the nature of the electrostatic accumulator and/or the nature of the lubricant oil provides a background level for the Total Color Difference value. This shows the potential benefit of comparing a Total Color Difference value obtained during/after activation of an electrostatic accumulator with a Total Color Difference value for a reference state that corresponds to no oil or "clean oil", so that background or inherent color differences can be subtracted out from differences due to the tendency of the oil to form additional deposits due to deterioration of the oil.

As shown in FIG. 2, exposure to a clean oil and exposure to an oil known to form light deposits resulted in similar Total Color Difference values after 20 hours of exposure. The oils that were known to produce medium or heavy deposits resulted in substantially higher Total Color Difference values. FIG. 2 demonstrates that applying a suitable potential across an electrostatic accumulator can produce a detectable change in Total Color Difference value after a period of time of less than a day. Based on this, the change in Total Color Difference value over the course of a given time period can be correlated with the amount of deposits that can accumulate over a longer time period.

Figure 3:
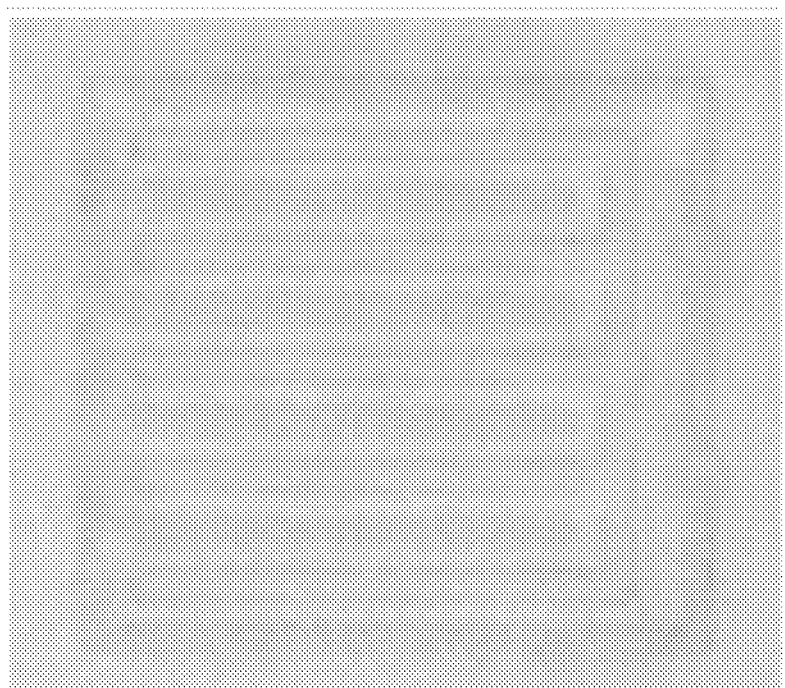
FIG. 3 shows an image of an electrostatic accumulator after exposure to a lubricant oil with some tendency to form deposits over time.
Figure 4:
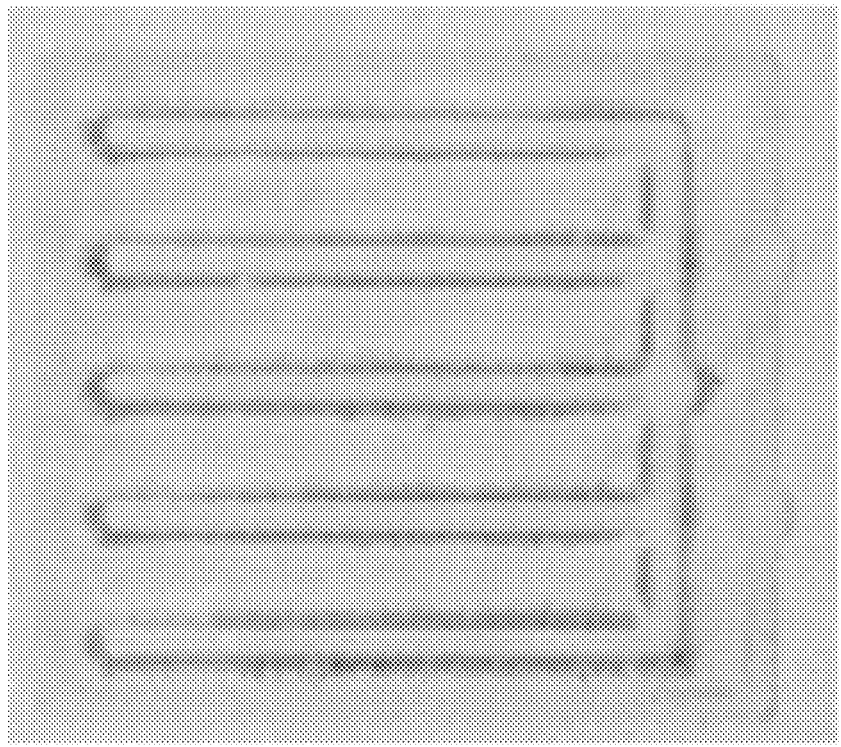
FIG. 4 shows an image of an electrostatic accumulator after exposure to a lubricant oil with some tendency to form deposits over time.
Figure 5:
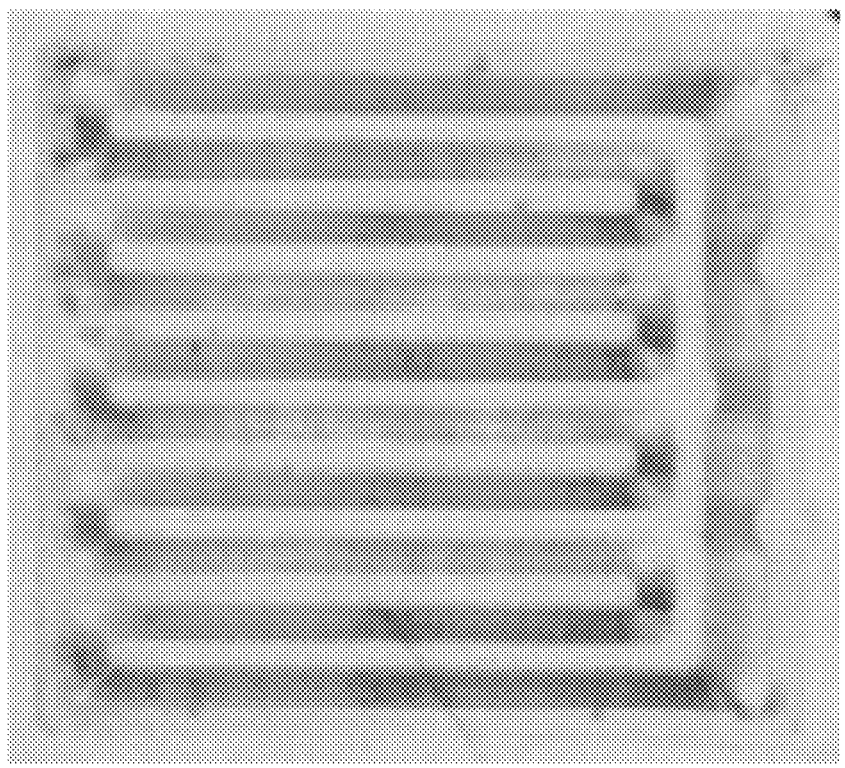
FIG. 5 shows an image of an electrostatic accumulator after exposure to a lubricant oil with some tendency to form deposits over time.

FIGS. 3 to 5 show images of the electrostatic accumulators after exposure for 1200 minutes (20 hours) to the oils that were known to form light, medium, and heavy deposits. As shown in FIG. 3, the image of the accumulator exposed to the oil with light deposit formation resulted in only minor differences relative to the clean oil image in FIG. 2. FIG. 4 shows more pronounced visual differences for the oil known to form medium deposits, while the oil known to form heavy deposits resulted in still larger contrast as shown in FIG. 5. Thus, the images in FIGS. 3 to 5 indicate that the Total Color Difference values shown in FIG. 2 can also be observed visually.

Figure 6:
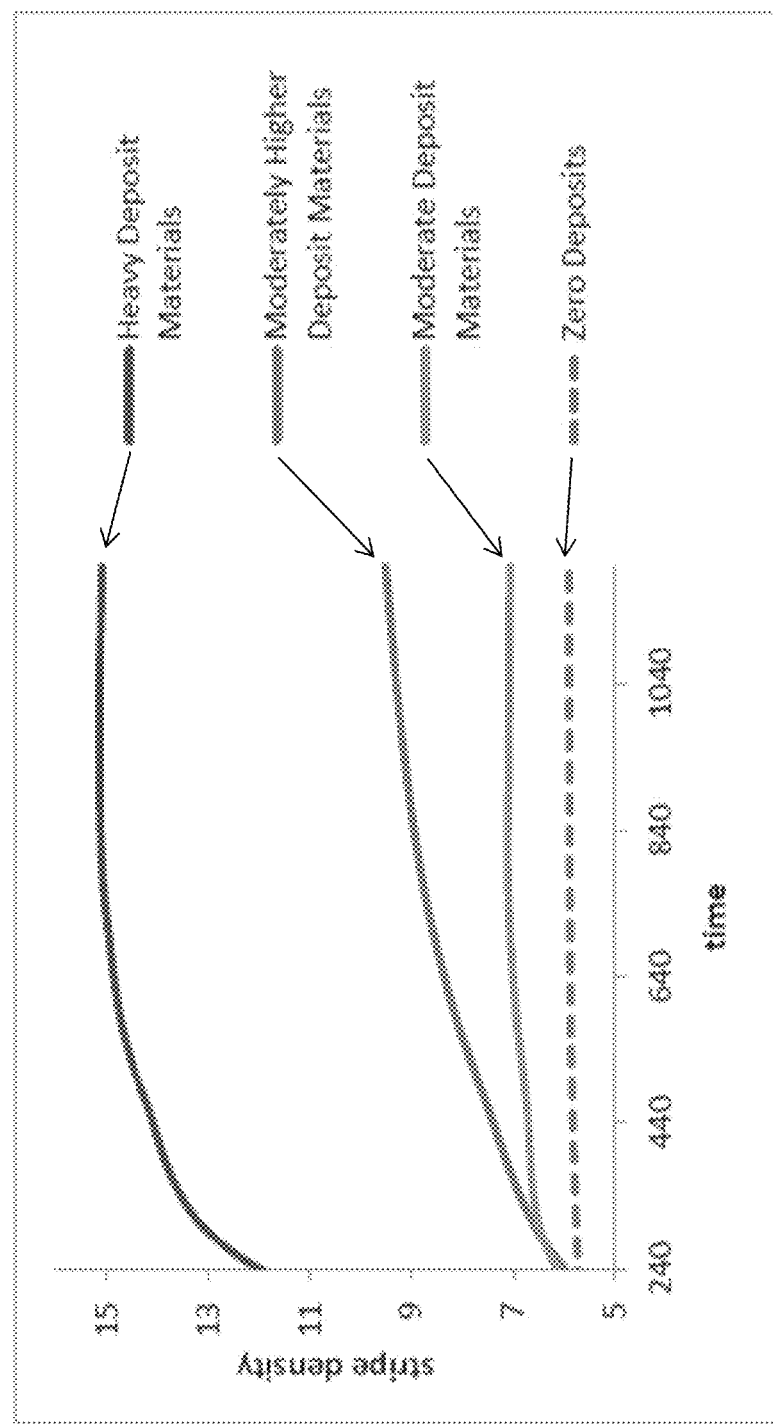
FIG. 6 shows strip density for electrostatic accumulators exposed to various lubricant oils while a potential difference is applied to the electrostatic accumulator

Additionally or alternately, other methods can be used to characterize images similar to those shown in FIGS. 3 to 5 in relation to a clean image of the electrostatic accumulator (such as the image shown in FIG. 1). For example, strip density is another conventional metric for characterizing the differences between images. Strip density corresponds to a characterization of the thickness and depth of color development between images, and can be correlated with a Total Color Difference value. To determine strip density, a photo is taken of accumulated varnish on an electrostatic accumulator and then compared with a white background. FIG. 6 shows strip density for the clean image and for images of an electrostatic accumulator after exposure to three lubricant oils with varying known tendencies for deposit accumulation. The "moderate deposit" line in FIG. 6 corresponds to the "moderate deposit" line in FIG. 2, while the "heavy deposit" line in FIG. 6 corresponds to the "heavy deposit" line in FIG. 2. The "light deposit" line from FIG. 2 is not represented in FIG. 6, due to the similarity under optical detection of the light deposit lubricant oil and a clean lubricant oil. An additional line for a "moderately heavy" lubricant oil is also shown in FIG. 6.

Similar to FIG. 2, the strip density of optical images of the electrostatic accumulator can be used to quantify the differences between oils with varying degrees of tendency to cause deposit accumulation. The strip density also shows the asymptotic behavior, so that a relatively short activation and measurement time can be used to characterize the tendency of a lubricant oil to accumulate deposits in-situ.

Figure 7:
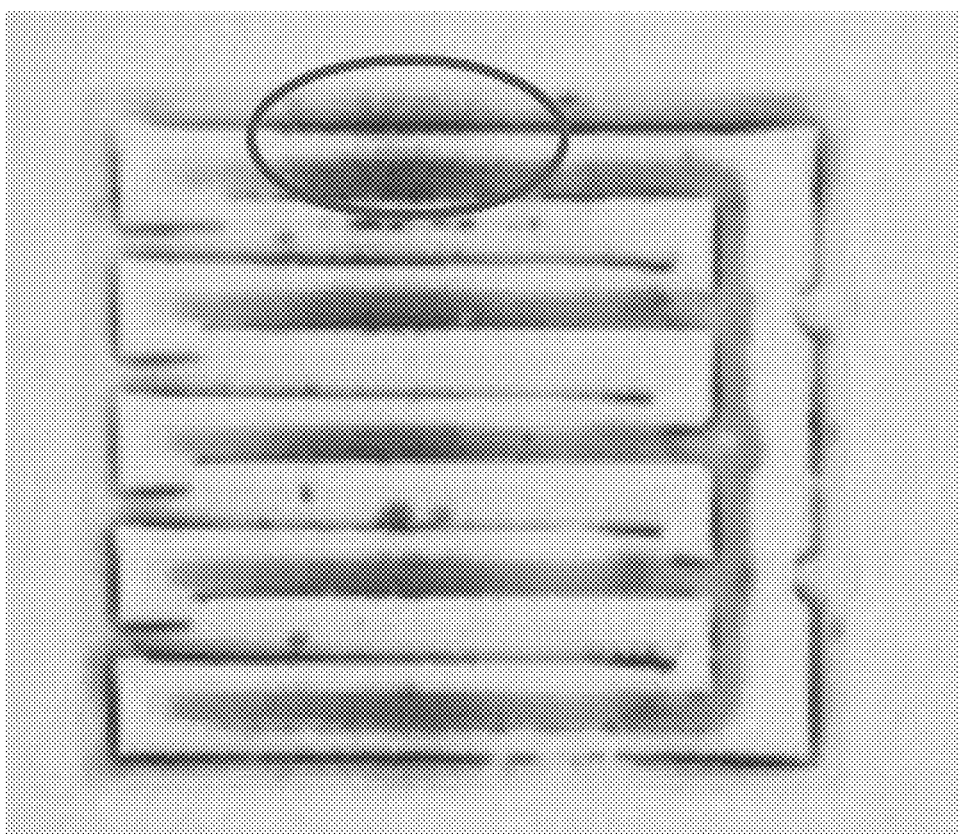
FIG. 7 shows an image of an electrostatic accumulator after exposure to a lubricant oil with some tendency to form deposits over time.

As another example, FIG. 7 shows an image of the electrostatic accumulator after exposure of the electrostatic accumulator to the "heavy deposit" lubricant oil after 20 hours of exposure, but at a higher potential difference than the image in FIG. 5. At the higher potential difference, the electric field of the electrostatic accumulator was sufficient to allow for alignment of iron deposits that accumulated on the surface. This can be seen, for example, inside of the circled area of the image in FIG. 7, where the accumulated deposits appear to correspond to a series of lines that are aligned with the electric field.

Alternative Characterization Methods

In addition to optical characterization using Total Color Difference, an electrostatic accumulator can be used in combination with other characterization methods to determine the potential for deposit formation of an oil in a lubricating environment. For example, an electrostatic accumulator can be incorporated as part of a quartz crystal microbalance (QCM). The QCM can be used to determine, for example, the rate of gain in mass due to enhanced deposit accumulation. Another option can be to monitor electrical characteristics on a sensor associated with the electrostatic accumulator, such as changes in conductivity, dielectric constant, and/or or impedance within a target frequency range. Still another option can be to use infrared and/or ultraviolet monitoring to attempt to characterize accumulation of deposits with specific types of compositions and/or functional groups. Yet another option can be to perform particle counting on particles that are deposited on the electrostatic accumulator.

ADDITIONAL EMBODIMENTS

Embodiment 1

A method for characterizing a lubricant oil in a lubricating environment, comprising: passing a lubricant oil through a volume in a lubricating environment, the volume having a surface comprising an electrostatic accumulator; applying, while passing the lubricant oil through the volume in the lubricating environment, a potential difference between at least a first portion of the electrostatic accumulator and a second portion of the electrostatic accumulator for a measurement period of time; characterizing, after the measurement period of time, at least a portion of the electrostatic accumulator while maintaining the electrostatic accumulator as a surface of the volume in the lubricating environment.

Embodiment 2

The method of any of the above embodiments, wherein characterizing the at least a portion of the electrostatic accumulator comprises optical characterization, mechanical characterization, electrical characterization, or a combination thereof.

Embodiment 3

The method of any of the above embodiments, wherein characterizing the at least a portion of the electrostatic accumulator comprises characterizing the first portion of the electrostatic accumulator, characterizing the second portion of the electrostatic accumulator, or a combination thereof.

Embodiment 4

The method of any of the above embodiments, wherein characterizing the at least a portion of the electrostatic accumulator comprises determining a Total Color Difference value, determining a strip density, or a combination thereof.

Embodiment 5

The method of Embodiment 4, wherein characterizing the at least a portion of the electrostatic accumulator further comprises comparing the Total Color Difference value to one or more threshold values.

Embodiment 6

The method of Embodiment 4 or 5, wherein determining a Total Color Difference value comprises determining a Total Color Difference relative to a white object-color stimulus.

Embodiment 7

The method of any Embodiments 4 to 6, wherein characterizing the at least a portion of the electrostatic accumulator comprises determining a change in a Total Color Difference value relative to a Total Color Difference value for a reference state of the electrostatic accumulator.

Embodiment 8

The method of Embodiment 7, wherein the Total Color Difference value for the reference state is determined at a time prior to the measurement period of time or determined at a time during the measurement period of time.

Embodiment 9

The method of Embodiment 7 or 8, wherein the reference state comprises an intermediate reference state that is different from a first reference state, the intermediate reference state having a Total Color Difference value that is 1.0 or more greater than a Total Color Difference value of the first reference state, or 10 or more greater, or 100 or more greater.

Embodiment 10

The method of any of the above embodiments, wherein the lubricating environment comprises at least one of an engine environment, a turbine environment, and a machine environment.

Embodiment 11

The method of any of the above embodiments, wherein the measurement period of time is 0.5 hours to 48 hours, or 0.5 hours to 24 hours, or 2 hours to 24 hours.

Embodiment 12

The method of any of the above embodiments, further comprising: removing the potential difference between at least the first portion of the electrostatic accumulator and the second portion of the electrostatic accumulator for an interim period of time while passing the lubricant oil through the volume in the lubricating environment; applying, while passing the lubricant oil through the volume in the lubricating environment, the potential difference between at least the first portion of the electrostatic accumulator and the second portion of the electrostatic accumulator for a second measurement period of time; and characterizing, after the second measurement period of time, the at least a portion of the electrostatic accumulator while maintaining the electrostatic accumulator as a surface of the volume in the lubricating environment.

Embodiment 13

The method of Embodiment 12, wherein characterizing the at least a portion of the electrostatic accumulator after the measurement period of time comprises determining a Total Color Difference value for a reference state of the electrostatic accumulator, and wherein characterizing the at least a portion of the electrostatic accumulator after the second measurement period of time comprises determining a change in a Total Color Difference value relative to the Total Color Difference value of the reference state, the reference state optionally comprising an intermediate reference state corresponding to a measurement time during the removing of the potential difference.

Embodiment 14

The method of any of the above embodiments, wherein the volume in the lubricating environment comprises a side stream volume or slip stream volume in the lubricating environment.

Embodiment 15

The method of any of the above embodiments, wherein characterizing the at least a portion of the electrostatic accumulator comprises characterizing a change in mass of the electrostatic accumulator using a quartz crystal microbalance; or wherein characterizing the at least a portion of the electrostatic accumulator comprises characterizing based on a conductivity, a dielectric constant, or an impedence in a target frequency range; or wherein characterizing the at least a portion of the electrostatic accumulator comprises characterizing based on infrared spectroscopy or ultraviolet spectroscopy; or wherein characterizing the at least a portion of the electrostatic accumulator comprises characterizing by performing particle counting; or a combination thereof.

When numerical lower limits and numerical upper limits are listed herein, ranges from any lower limit to any upper limit are contemplated. While the illustrative embodiments of the invention have been described with particularity, it will be understood that various other modifications will be apparent to and can be readily made by those skilled in the art without departing from the spirit and scope of the invention. Accordingly, it is not intended that the scope of the claims appended hereto be limited to the examples and descriptions set forth herein but rather that the claims be construed as encompassing all the features of patentable novelty which reside in the present invention, including all features which would be treated as equivalents thereof by those skilled in the art to which the invention pertains.

The present invention has been described above with reference to numerous embodiments and specific examples. Many variations will suggest themselves to those skilled in this art in light of the above detailed description. All such obvious variations are within the full intended scope of the appended claims.

The invention claimed is:

1. A method for characterizing a lubricant oil in a lubricating environment, comprising:
   passing a lubricant oil through a volume in a lubricating environment, the volume having a surface comprising an electrostatic accumulator;
   applying, while passing the lubricant oil through the volume in the lubricating environment, a potential difference between at least a first portion of the electrostatic accumulator and a second portion of the electrostatic accumulator for a measurement period of time;
   characterizing, after the measurement period of time, at least a portion of the electrostatic accumulator while maintaining the electrostatic accumulator as a surface of the volume in the lubricating environment wherein characterizing the at least a portion of the electrostatic accumulator comprises optical characterization as measured on the surface of the electrostatic accumulator.

2. The method of claim 1, wherein characterizing the at least a portion of the electrostatic accumulator comprises characterizing the first portion of the electrostatic accumulator, characterizing the second portion of the electrostatic accumulator, or a combination thereof.

3. The method of claim 1, wherein characterizing the at least a portion of the electrostatic accumulator comprises determining a Total Color Difference value as measured on the surface of the electrostatic accumulator.

4. The method of claim 3, wherein characterizing the at least a portion of the electrostatic accumulator further comprises comparing the Total Color Difference value as measured on the surface of the electrostatic accumulator to one or more threshold values.

5. The method of claim 3, wherein determining a Total Color Difference value as measured on the surface of the electrostatic accumulator comprises determining a Total Color Difference relative to a white object-color stimulus.

6. The method of claim 3, wherein characterizing the at least a portion of the electrostatic accumulator comprises determining a change in a Total Color Difference value as measured on the surface of the electrostatic accumulator relative to a Total Color Difference value for a reference state of the electrostatic accumulator.

7. The method of claim 6, wherein the Total Color Difference value as measured on the surface of the electrostatic accumulator for the reference state is determined at a time prior to the measurement period of time or determined at a time during the measurement period of time.

8. The method of claim 6, wherein the reference state comprises an intermediate reference state that is different from a first reference state, the intermediate reference state having a Total Color Difference value as measured on the surface of the electrostatic accumulator that is 1.0 or more greater than a Total Color Difference value of the first reference state.

9. The method of claim 3, further comprising:
determining, at a first time, a first Total Color Difference value for at least a portion of the electrostatic accumulator while maintaining the electrostatic accumulator as a surface of the volume in the lubricating environment;
determining, at a second time after the measurement period of time, a second Total Color Difference value for the at least a portion of the electrostatic accumulator while maintaining the electrostatic accumulator as a surface of the volume in the lubricating environment; and
comparing the second Total Color Difference value with the first Total Color Difference value.

10. The method of claim 1, wherein characterizing the at least a portion of the electrostatic accumulator comprises determining a strip density wherein a photo is taken of the accumulated varnish on the electrostatic accumulator and then compared with a white background.

11. The method of claim 1, wherein the lubricating environment comprises at least one of an engine environment, a turbine environment, and a machine environment.

12. The method of claim 1, wherein the measurement period of time is 0.5 hours to 48 hours.

13. The method of claim 1, further comprising:
removing the potential difference between at least the first portion of the electrostatic accumulator and the second portion of the electrostatic accumulator for an interim period of time while passing the lubricant oil through the volume in the lubricating environment;
applying, while passing the lubricant oil through the volume in the lubricating environment, the potential difference between at least the first portion of the electrostatic accumulator and the second portion of the electrostatic accumulator for a second measurement period of time; and
characterizing, after the second measurement period of time, the at least a portion of the electrostatic accumulator while maintaining the electrostatic accumulator as a surface of the volume in the lubricating environment.

14. The method of claim 13, wherein characterizing the at least a portion of the electrostatic accumulator after the measurement period of time comprises determining a Total Color Difference value for a reference state of the electrostatic accumulator, and wherein characterizing the at least a portion of the electrostatic accumulator after the second measurement period of time comprises determining a change in a Total Color Difference value relative to the Total Color Difference value of the reference state.

15. The method of claim 13, wherein the reference state comprises an intermediate reference state; the intermediate reference state corresponding to a measurement time during the removing of the potential difference.

16. The method of claim 1, wherein the volume in the lubricating environment comprises a side stream volume or slip stream volume in the lubricating environment.

17. The method of claim 9, wherein the first time is prior to the measurement period of time, or wherein the first time is during the measurement period of time.

18. The method of claim 3, further comprising:
determining, after the first measurement period of time, a first Total Color Difference value for at least a portion of the electrostatic accumulator while maintaining the electrostatic accumulator as a surface of the volume in the lubricating environment;
removing, after the first measurement period of time, the potential difference between at least the first portion of the electrostatic accumulator and the second portion of the electrostatic accumulator for an interim period of time while passing the lubricant oil through the volume in the lubricating environment;
applying, after the interim period of time, while passing the lubricant oil through the volume in the lubricating environment, the potential difference between at least the first portion of the electrostatic accumulator and the second portion of the electrostatic accumulator for a second measurement period of time;
determining, after the second measurement period of time, a second Total Color Difference value for the at least a portion of the electrostatic accumulator while maintaining the electrostatic accumulator as a surface of the volume in the lubricating environment; and
comparing the second Total Color Difference value with the first Total Color Difference value.

* * * * *